(12) United States Patent
Izatt et al.

(10) Patent No.: US 7,602,500 B2
(45) Date of Patent: Oct. 13, 2009

(54) OPTICAL COHERENCE IMAGING SYSTEMS HAVING A REDUCED EFFECTIVE LINEWIDTH AND METHODS OF USING THE SAME

(75) Inventors: Joseph A. Izatt, Raleigh, NC (US); Eric L. Buckland, Hickory, NC (US); William J. Brown, Durham, NC (US)

(73) Assignee: Bioptigen, Inc., Durham, NC (US)

( * ) Notice: Subject to any disclaimer, the term of this patent is extended or adjusted under 35 U.S.C. 154(b) by 218 days.

(21) Appl. No.: 11/495,226

(22) Filed: Jul. 28, 2006

(65) Prior Publication Data

US 2007/0024856 A1 Feb. 1, 2007

Related U.S. Application Data

(60) Provisional application No. 60/703,376, filed on Jul. 28, 2005.

(51) Int. Cl.
*G01B 9/02* (2006.01)
(52) U.S. Cl. .................................... 356/497
(58) Field of Classification Search ................. 356/497, 356/479
See application file for complete search history.

(56) References Cited

U.S. PATENT DOCUMENTS

| 7,355,716 | B2* | 4/2008 | de Boer et al. | 356/479 |
|---|---|---|---|---|
| 7,391,520 | B2* | 6/2008 | Zhou et al. | 356/479 |
| 2001/0045513 | A1 | 11/2001 | Kourogi et al. | |
| 2004/0021922 | A1 | 2/2004 | Chen et al. | |
| 2005/0018201 | A1 | 1/2005 | de Boer et al. | 356/479 |
| 2007/0002327 | A1 | 1/2007 | Zhou et al. | |

OTHER PUBLICATIONS

International Search Report and Written Opinion for PCT/US2006/029313; date of mailing Mar. 5, 2007.
Choma et al. "Swept source optical coherence tomography using an all-fiber 1300-nm ring laser source" *Journal of Biomedical Optics* 10(4):044009-1-044009-6 (2005).
Invitation to Pay Additional Fees for PCT/US2006/029313; date of mailing Jan. 2, 2007.
Hu et al. "Enhancement of FDOCT Imaging Range by Sub-Pixel Spectral Shifting" *Conference on Lasers & electro-Optics (CLEO)* 2067-2069 (2005).
Konoshita et al., "Optical frequency-domain imaging microprofilometry with a frequency-tunable liquid-crystal Fabry-Perot etalon device" *Applied Optics* 38:34 7063-7068 (1999).
Lee et al. "Ultrahigh Scanning Speed Optical Coherence Tomography Using Optical Frequency Comb Generators" *Jpn. J. Appl. Phys.* 40L878-L880 (2001).
Oh et al. "Optical Frequency-Domain Reflectometry Based on Wavelength-Swept Mode-Locked Fiber Laser" *IEEE Photonics Technology Letters* 15(2):266-268 (2003).

(Continued)

*Primary Examiner*—Hwa (Andrew) S Lee
(74) *Attorney, Agent, or Firm*—Myers Bigel Sibley & Sajovec

(57) ABSTRACT

Frequency domain optical coherence imaging systems have an optical source, an optical detector and an optical transmission path between the optical source and the optical detector. The optical transmission path between the optical source and the optical detector reduces an effective linewidth of the imaging system. The optical source may be a broadband source and the optical transmission path may include a periodic optical filter.

32 Claims, 15 Drawing Sheets

OTHER PUBLICATIONS

Zhao et al. "Optical frequency-domain reflectometry (OFDR) using an integrated fiber tunable filter" *SPIE* 3598: 56-60 (1999).

Tan-no et al., "Optical multimode frequency-domain reflectometer", Optics Letters, vol. 19, No. 8, Apr. 15, 1994, 587-589.

Yun et al., "High-speed spectral-domain optical coherence tomography at 1.3 μm wavelength", Optics Express, vol. 11, No. 26, Dec. 29, 2003, 3598-3604.

Leitgeb et al., "Performance of fourier domain vs. time domain optical coherence tomography", Optics Express, vol. 11, No. 8, Apr. 21, 2003, 889-894.

Choma et al., "Sensitivity advantage of swept source and Fourier domain optical coherence tomography", Optics Express, vol. 11, No. 18, Sep. 8, 2003, 2183-2189.

Dorrer et al., Spectral resolution and sampling issues in Fourier-transformation spectral interferometry, J. Opt. Soc. Am. B, vol. 17, No. 10, Oct. 2000, 1795-1802.

Hausler et al., "'Coherence Radar' and 'Spectral Radar'—New Tools for Dermatological Diagnosis", Journal of Biomedical Optics, vol. 3, No. 1, 21-31, Jan.1998.

\* cited by examiner

OPTICAL COHERENCE IMAGING SYSTEMS HAVING A REDUCED EFFECTIVE LINEWIDTH AND METHODS OF USING THE SAME

RELATED APPLICATIONS

The present application claims priority from U.S. Provisional Application No. 60/703,376, filed Jul. 28, 2005, the disclosure of which is hereby incorporated herein in its entirety by reference.

BACKGROUND OF THE INVENTION

The present invention relates to imaging systems and, more particularly, to optical-coherence imaging systems.

A variety of approaches to imaging using optical coherence tomography (OCT) are known. Such systems may be characterized as Fourier domain OCT (FD-OCT) and time domain OCT (TD-OCT). FD-OCT generally includes swept source (SS) and spectral domain (SD), where SD systems generally use a broadband source in conjunction with a spectrometer rather than a swept laser source and a photodiode(s). TD systems generally rely on movement of a mirror or reference source over time to control imaging depth by providing coherence depth gating for the photons returning from the sample being imaged. Both systems use broadband optical sources, producing a low aggregate coherence that dictates the achievable resolution in the depth, or axial, direction.

These imaging techniques are derived from the general field of Optical Low Coherence Reflectometry (OLCR). The time domain techniques are specifically derived from Optical Coherence Domain Reflectometry. Swept source techniques are specifically derived from Optical Frequency Domain Reflectometry. Spectral domain techniques have been referred to as "spectral radar."

In contrast to time domain systems, in FD-OCT the imaging depth may be determined by Fourier transform relationships between the acquired spectrum, rather than by the range of a physically scanned mirror, thereby allowing concurrent acquisition of photons from all imaged depths in the sample. Specifically, in FD-OCT, the optical frequency interval between sampled elements of the spectrum may be used to control the imaging depth, with a narrower sampling interval providing a deeper imaging capability.

In addition to total bandwidth, which generally controls the axial resolution, and sampling interval, which generally controls the imaging depth, a third parameter, the effective sampled linewidth, generally controls a quality of the image as function of depth. As used herein, references to "linewidth" refer to the effective sampled linewidth unless indicated otherwise. As the effective sampled linewidth at each sampled interval is increased, the effective sampled coherence length decreases, which may produce a detrimental envelope of decreasing signal-to-noise ratio across the imaged depth. This behavior is commonly known as fall-off and it is generally desirable to minimize this signal quality fall-off.

SUMMARY OF THE INVENTION

Embodiments of the present invention include frequency domain optical coherence imaging systems having an optical source, an optical detector and an optical transmission path between the optical source and the optical detector. The optical transmission path between the optical source and the optical detector reduces an effective linewidth of the imaging system. The optical source may be a broadband or low coherence source and the optical transmission path may include a periodic optical filter.

In other embodiments, the optical detector is a plurality of optical detectors and the optical transmission path includes a spatial mask positioned proximate the optical detectors. The plurality of optical detectors may be a spectrometer and the spatial mask may be positioned in the spectrometer. The spectrometer may be a tunable spectrometer.

In further embodiments, the optical source is a broadband source and the optical transmission path includes an optical splitter having a first side including a port coupled to a source arm and a port coupled to a detector arm and a second side having a port coupled to a reference arm and a port coupled to a sample arm. The optical transmission path further includes a periodic optical filter. The periodic optical filter may be positioned in the detector arm between the optical splitter and the optical detector. The optical detector may be a first spectrometer and a second spectrometer and the periodic optical filter may have a first output coupled to the first spectrometer and a second output coupled to the second spectrometer. The periodic optical filter may be an interleaver having a finesse of two or of greater than two. The periodic optical filter may have a free spectral range that substantially matches a pixel spacing of the first and second spectrometer.

In other embodiments, the optical detector is a spectrometer and the system further includes an optical switching device in the detector arm that selectively couples a plurality of outputs of the periodic optical filter to the spectrometer. The periodic optical filter may be an interleaver having a finesse of two and the plurality of outputs of the periodic filter may be a first comb output and a second comb output, each having substantially equal peak widths and the second comb output may be offset from the first comb output by about half of a free spectral range of the periodic optical filter.

In yet further embodiments, the periodic optical filter is a cascaded plurality of optical filters and the optical detector is a first spectrometer and a second spectrometer. The cascaded periodic optical filters have a first output coupled to the first spectrometer and a second output coupled to the second spectrometer. The first output may be a first set of outputs from one of the cascaded periodic optical filters and the second output may be a second set of outputs from another of the cascaded periodic optical filters. The system may further include a first optical switching device coupling the first set of outputs to the first spectrometer and a second optical switching device coupling the second set of outputs to the second spectrometer. The cascaded periodic filters may be configured to generate the first and second set of outputs by splitting an optical signal input into a plurality of combs that are periodic and offset from each other. The first and second spectrometer may have a pixel spacing substantially equal to a largest free spectral range of the cascaded periodic optical filters. The cascaded periodic optical filters may include at least one output not coupled to the first or the second spectrometer and an image falloff of the system may be determined based on a filter width of a narrowest of the periodic optical filters and a falloff of the system may be determined based on a minimum optical interval between pixels of the optical detector.

In other embodiments, the periodic optical filter is a tunable periodic optical filter having a selectable output wavelength comb spectra. The tunable periodic optical filter may have a selectable free spectral range and/or finesse. The tunable periodic optical filter may have a tuning rate selected based on a desired image rate for the system. The tunable periodic optical filter may have a number of steps in a scan selected to provide a desired resolution and/or falloff.

In further embodiments, the periodic optical filter is positioned in the source arm between the optical splitter and the optical source.

In yet other embodiments, the system further includes a second periodic optical filter. The first periodic optical filter is positioned in the reference arm or the sample arm and the second periodic optical filter is positioned in a different arm of the system. The periodic optical filters may be interleavers having a substantially same free spectral range (FSR) and a finesse of at least two and the periodic optical filters may be offset by about one quarter of the FSR. One or both of the periodic optical filters may be a tunable periodic optical filter.

In other embodiments, the optical source is a plurality of tunable optical sources and the optical detector is a plurality of optical detectors, ones of which are optically coupled to respective ones of the tunable optical sources by the optical transmission path. The optical transmission path may include an optical multiplexer coupling the plurality of tunable optical sources to a source arm of the system and an optical demultiplexer coupling the plurality of optical detectors to a detector arm of the system. A periodic optical filter may be provided in the source arm, the detector arm, a sample arm of the system and/or a reference arm of the system.

In yet further embodiments, the optical source includes super luminescent diode sources and the optical detectors are spectrometers, ones of which are optically coupled to a selected wavelength range emitted by the super luminescent diode sources. The optical transmission path may include an optical multiplexer coupling the super luminescent diode sources to a source arm of the system and an optical demultiplexer coupling the spectrometers to a detector arm of the system. A periodic optical filter may be provided in the source arm, the detector arm, a sample arm of the system and/or a reference arm of the system.

In other embodiments, the optical source includes a plurality of optical sources and the optical detector includes a plurality of optical detectors. The optical transmission path includes an optical splitter having a first side including a port coupled to a source arm and a second side having a port coupled to a reference arm and a port coupled to a sample arm and an optical multiplexer/demultiplexer coupling the plurality of optical sources and optical detectors to the source arm. The plurality of optical sources and optical detectors may be a plurality of optical source and detector pairs and the optical transmission path may further include a plurality of circulators coupling respective ones of the optical source and detector pairs to the optical multiplexer/demultiplexer.

In further embodiments, the optical source is a broadband source and the optical detector is a spectrometer. The optical transmission path includes an optical splitter having a first side including a port coupled to the spectrometer and a second side having a port coupled to a reference arm and a port coupled to a sample arm and a periodic optical filter arrangement coupling the sample arm and the reference arm to the broadband source. The optical splitter may be a first optical splitter and the periodic optical filter arrangement may include a first periodic optical filter coupled to the reference arm and a second periodic optical filter coupled to the sample arm. A second optical splitter may be provided having a first side including a port coupled to the broadband source and a second side including a port coupled to the first periodic optical filter and a second port coupled to the second periodic optical filter. The first periodic optical filter and the first optical splitter may be coupled to the reference arm by a first circulator and the second periodic optical filter and the first optical splitter may be coupled to the sample arm by a second circulator.

In yet other embodiments, optical coherence imaging systems include an optical splitter, an optical source and an optical detector. The optical splitter has a first side including a port coupled to a source arm and a port coupled to a detector arm and a second side having a port coupled to a reference arm and a port coupled to a sample arm. The optical source is coupled to the source arm and generates a comb output having an associated spacing and linewidth. The optical detector is coupled to the detector arm. The optical detector has a spacing and a bandwidth selected based on the associated spacing and linewidth of the optical source to reduce an effective linewidth of the imaging system.

DETAILED DESCRIPTION OF THE INVENTION

Figure 1:
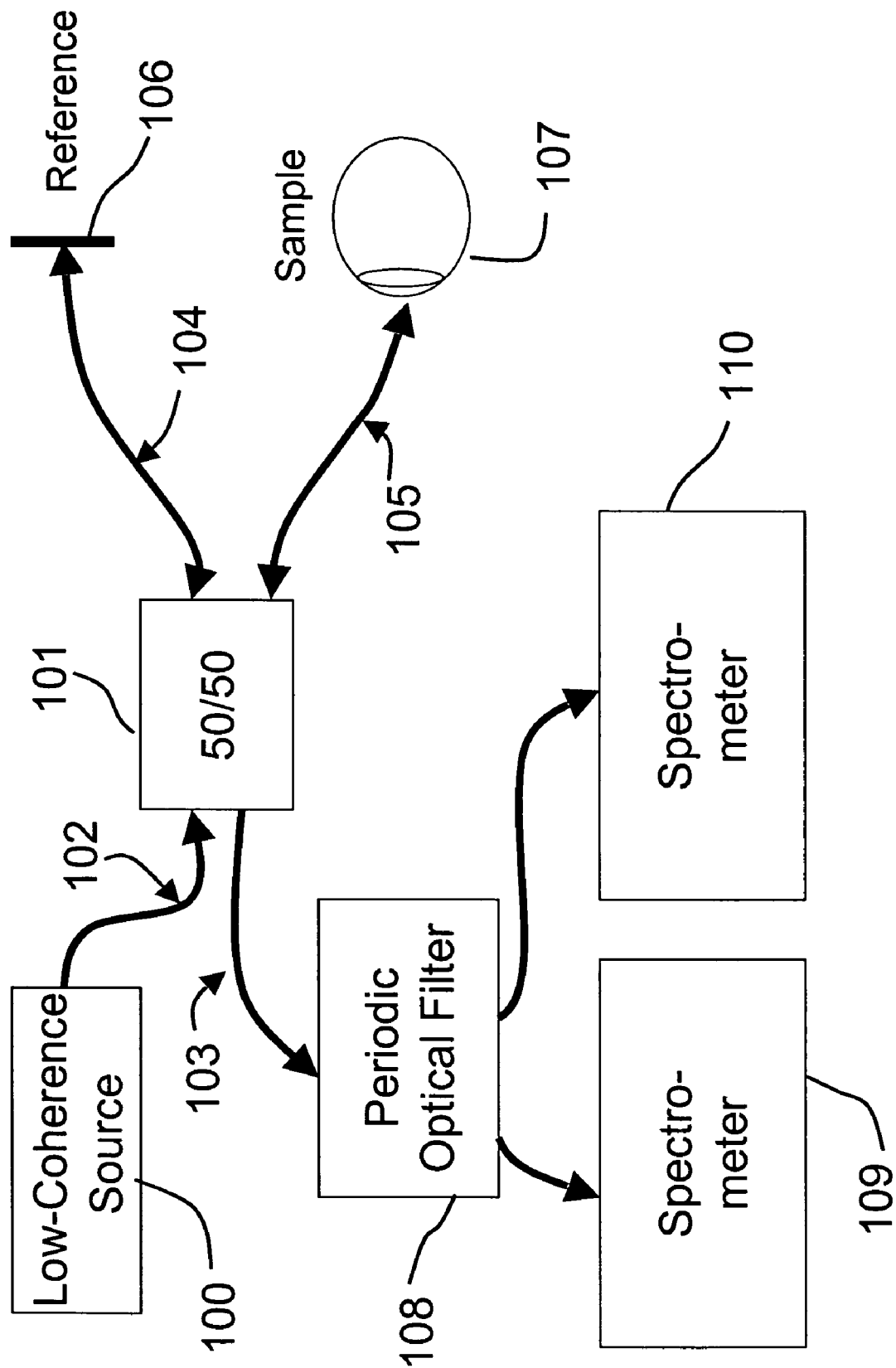
FIG. 1 is a schematic block diagram illustrating an optical engine (system) according to some embodiments of the present invention.

Specific exemplary embodiments of the invention now will be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the particular exemplary embodiments illustrated in the accompanying drawings is not intended to be limiting of the invention. In the drawings, like numbers refer to like elements.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Some embodiments of the present invention provide optical systems (engines) for OCT that employ one or more optical filtering devices that may increase the image resolution, increase the image depth and/or reduce the image fall off. The filters may serve several functions including: ensuring that each individual detector sees one linewidth-managed source sample at any given moment; selecting what portion of the spectrum is seen by a spectrometer, and; shaping the bandwidth seen by each pixel inside any of the spectrometers. The advantages of adding filtering in some embodiments may include intrinsically superior image quality, improved performance with less expensive parts, improved fall-off by narrowing effective sampled linewidth, higher resolution systems enabled by multiple sources spanning longer wavelengths and higher imaging speed based on the further advantages of parallel data acquisition, which may enable shorter scanning ranges for swept sources or multiple spectrometers each acquiring data.

In some embodiments of the present invention an optical filter is added to an otherwise conventional OCT engine. Optical filters are devices that selectively pass light based on the physical properties of the light including the wavelength, wavemode, and/or polarization. Examples of optical filters include thin film filters, fiber Bragg gratings, dichroic filters, arrayed waveguide filters, Fabry Perot filters, echelle gratings, interleavers, bulk diffraction gratings and others. These devices are commercially available from numerous companies including large optical vendors, such as JDSU and Bookham.

Optical filters can be grouped into several categories including: Type 1, filters having one input and two outputs that separate out one band of wavelengths; Type 2, filters having one input and multiple outputs that separate out bands of wavelengths, and; Type 3, filters having one input and two outputs that separate wavelengths in a periodic fashion. Type 1 includes thin film filters, dichroic filters, and fiber Bragg gratings (with circulators). These filters are generally useful for adding or removing a particular wavelength from a group of wavelengths. By cascading these filters, multiple wavelengths may be combined or split apart although the insertion loss can limit the performance of the cascade.

Type 2 filters include arrayed waveguides (AWGs), echelle gratings, and bulk diffraction gratings. These filters generally split the input light into many wavelength groups with each group having its own output port. These filters are generally useful for combining or splitting many wavelengths with port counts up to 80 now available, and port counts up to 1080 have been reported. Spectrometers use this same principle with a bulk diffraction grating spreading the spectrum across an array of photodiodes instead of an array of output ports.

Type 3 filters are periodic filters that pass evenly spaced wavelengths out of one port and all other light out of the other port. Examples include Fabry Perot filters and interleavers. It is possible to build these devices with a wide range of wavelength spacing and finesses. Interleavers available in the telecommunications industry typically have a finesse of 2 and a periodicity ranging from 200 GHz down to 25 GHz in the 1550 nm telecommunications window (0.2 nm to 1.6 nm).

Also included in some embodiments of the present invention are optical switching devices (or optical switches). Numerous technology implementations for optical switches can be used, including, but not limited too, mechanical switches based on moving mirrors or prisms, micro-electro-mechanical systems (MEMS) based mirror switches, moving fiber switches, frustrated total internal reflection (FTIR) switches, switches based on phase changing, such as lithium niobate modulators, and switches based on thermal effects. Relevant parameters of the switches may include the insertion loss of the switch and the switching time.

Some embodiments of the present invention will now be described with reference to the schematic block diagrams of FIGS. 1-14. Referring first to the embodiments of FIG. 1, a periodic optical filter (POF) 108 is provided in the detector arm (path) 103 to split the spectrum into two combs having their associated spacing and width controlled by the characteristics of the POF 108. If a typical interleaver with a finesse of 2 is used as the POF 108, then there are two output combs that have substantially equal peak widths and are offset by one half of the free spectral range of the POF 108. One of the combs of wavelengths passes to the spectrometer 109 and the offset comb of wavelengths pass to the spectrometer 110. Other POFs may be used that pass less that one half the total bandwidth to one output of the POF and more that half the total bandwidth to the other output of the POF.

Also shown in the embodiments of FIG. 1 is a low coherent source 100 that provides the optical source to the source arm 102 to a polarization beam splitter (coupler) 101. However, it will be understood that, in some embodiments, a comb source may be used as the source 100 and the periodic optical filter 108 may be omitted. The splitter 101 provides the optical source light down a reference arm 104 to reference 106, such as a mirror, and the sample arm 105 to the sample 107, illustrated schematically as a human eye in FIG. 1. The detector arm 103 couples the periodic optical filter 108 to the splitter 101.

In some embodiments, the spectrometers 109 and 110 may be identical, but they need not be. In some embodiments, the pixels inside the spectrometers are only illuminated by half of the wavelengths that they would see without the POF. In other words, the free spectral range (FSR) of the POF 108 matches or nearly matches the pixel spacing, e.g. sampling interval, in the spectrometers 109 and 110.

The most common design of spectrometers generally results in pixels that are evenly spaced in wavelength, whereas typical POFs are evenly spaced in frequency. This may be advantageous given that the data out of the spectrometer is typically resampled from wavelength spacing to frequency spacing prior to further processing by the OCT engine. However, it will be understood that, in some embodiments, the POF 108 is evenly spaced in wavelength and the spectrometers 109 and 110 are evenly spaced in frequency, for example, by chirping the pixel spacing or using additional corrective optics inside the spectrometer.

This partial illumination of each pixel may reduce the effective acquisition linewidth of the pixel, which may decrease the fall off. In some embodiments of the present invention where an interleaver is used for the POF 108, one half of each pixel in the spectrometer may be illuminated and the fall off may be reduced by a factor of 2, independent of whether one or two spectrometers are used. If both spectrometers are used, the sampling interval is effectively reduce by half, which may double the total imaging depth into the sample as well.

Figure 2:
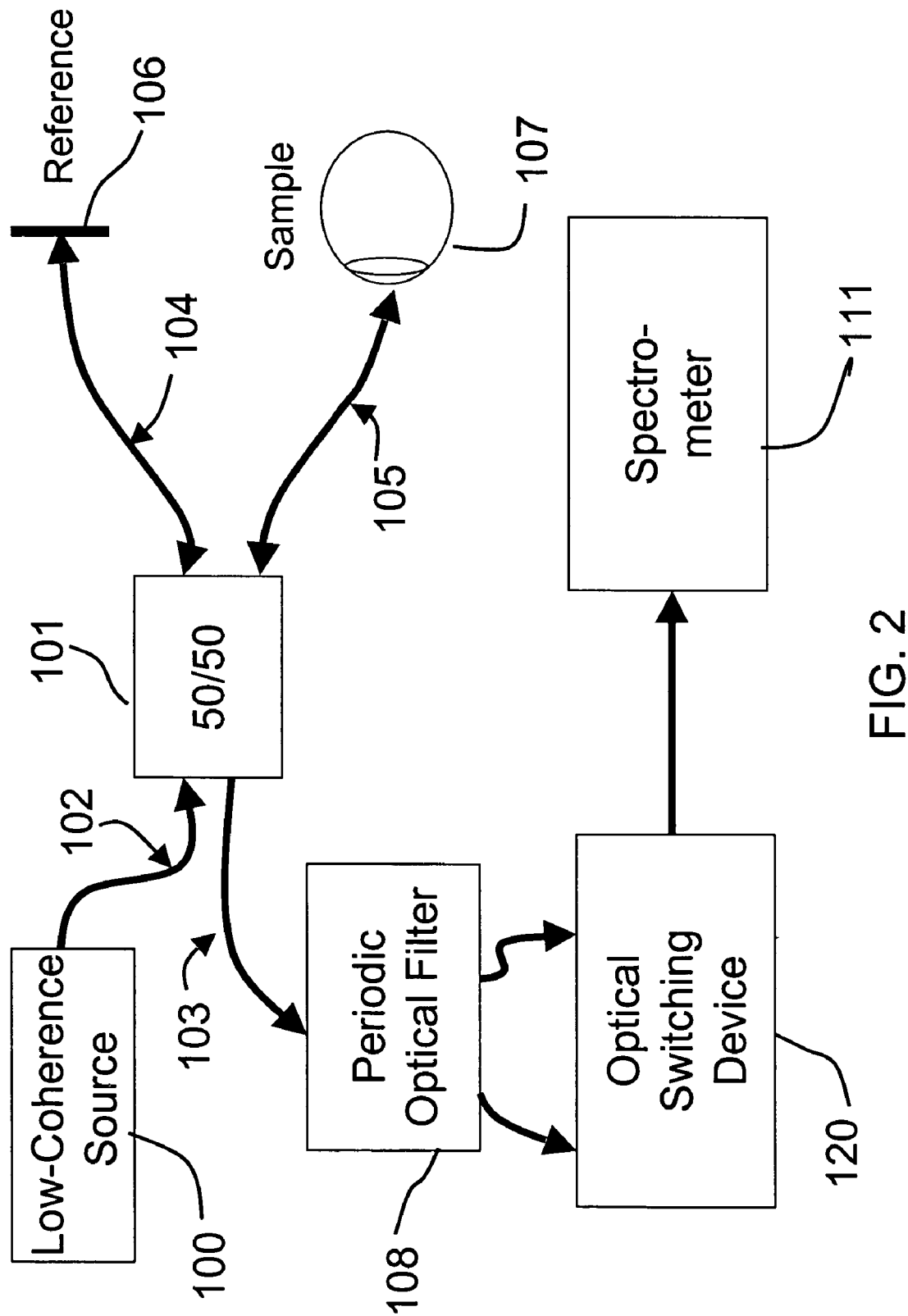
FIG. 2 is a schematic block diagram illustrating an optical engine (system) according to other embodiments of the present invention.

The embodiments illustrated in FIG. 2 similarly use a POF 108 but, instead of two spectrometers 109, 110, a single spectrometer 111 and an optical switching device 120 are used. This may have the same advantages of the configuration shown in FIG. 1 in that the fall off may be reduced by a factor of 2 and the depth may be increased by a factor of 2, but do so while only using one spectrometer. In typical implementations, the spectrometer 111 may represent a significant portion of the cost of the system and optical switching devices 120 may be cheaper. The optical switching device 120 may be selected so that it switches fast enough that the spectrometer 111 can still measure twice as many spectra in a given time and so that the optical switching device 120 has sufficient extinction ratio that light leaking through from the opposite input is not a significant noise source for the spectrometer 111.

Figure 3:
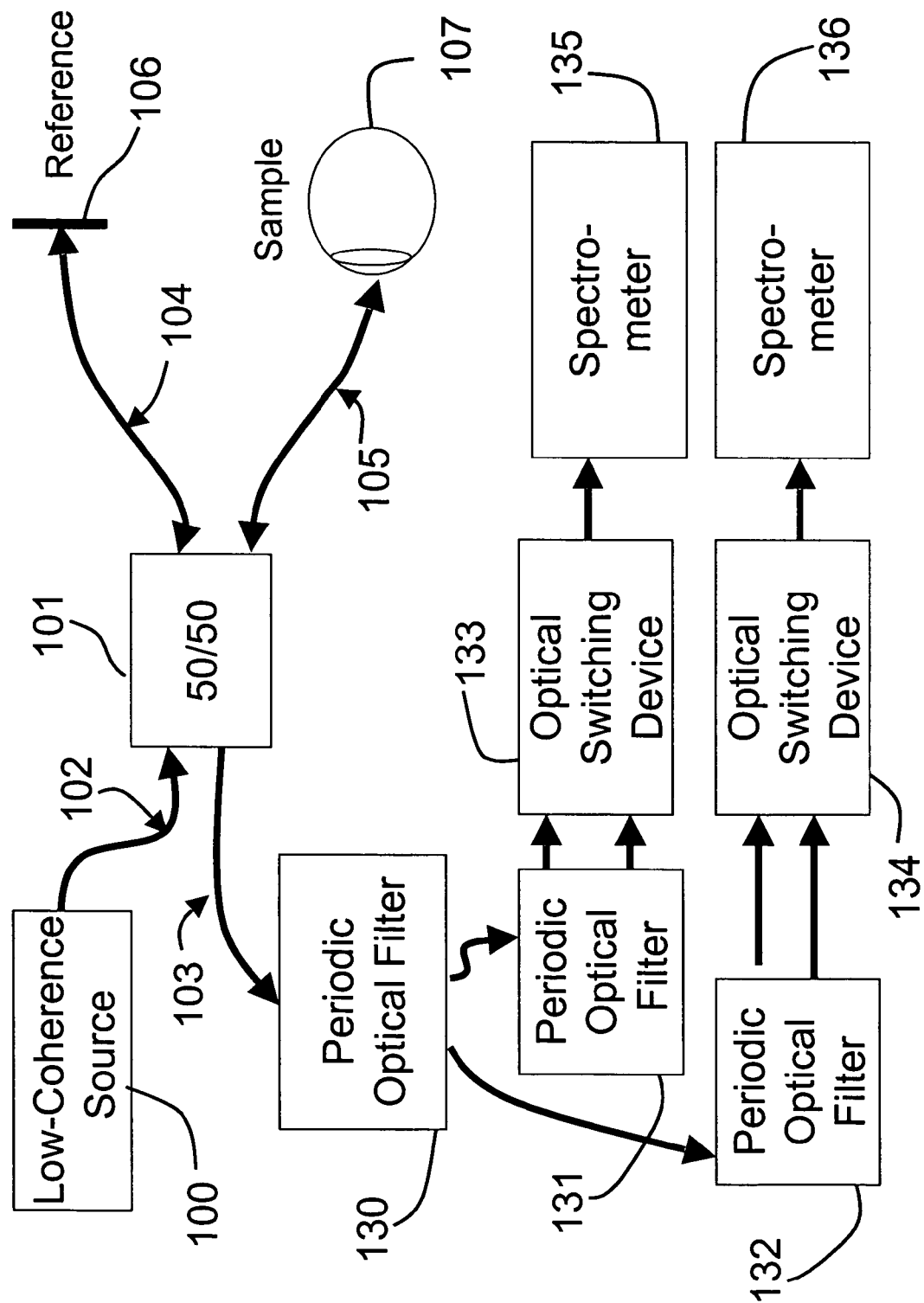
FIG. 3 is a schematic block diagram illustrating an optical engine (system) according to other embodiments of the present invention.

The embodiments illustrated in FIG. 3 include aspects from both embodiments previously described with reference to FIGS. 1 and 2. In the embodiments of FIG. 3 multiple POFs 130, 131 and 132 are used in conjunction with a combination of spectrometer(s) 135 and 136 and may, optionally, also include one or more optical switching devices 133 and 134. At least one spectrometer is used in the embodiments of FIG. 3, but the number of optical switching devices may range from none to a plurality. The cascaded POFs 130, 131 and 132 split the spectrum into multiple combs, where ones of the combs are periodic and offset from the other combs. In some embodiments, the POF 130 has a FSR that is half the FSR of POFs 131 and 132 and all the POFs having a finesse of 2. Such embodiments may split the incoming spectrum into four spectra, with the spacing for each spectra equal to the FSR of POFs 131 and 132 and peak widths determined by POFs 131 and 132. The ordering of the POFs may vary in some embodiments with a filter with each free spectral range present in each path.

Once the wavelengths are split into multiple combs, they pass to spectrometers 135 and 136 or through optical switching devices 133 and 134 to the spectrometers 135 and 136. In some embodiments, the spectrometers 135 and 136 have a pixel spacing equal to the largest free spectral range of the POFs. Note that the optical switching device 133 and 134 may have more than two inputs and one output, for example, an M×N optical switching device could be used to connect M outputs of POFs to N spectrometers. In other embodiments, the optical switching devices are not included and the outputs of the POFs 130, 131, 132 are connected directly to the spectrometer(s) 135, 136.

All of the outputs of the POF(s) may not be used and the image fall off may be determined by the filter width of the narrowest POF and the image depth may be set by the effective sampling interval, which depends on the number of spectrometers. In some embodiments, an upgradable system is provided where one or more POFs and one or more spectrometers and one or more optical switching devices are installed on day one and, as user requirements change, additional POFs, optical switching devices and/or spectrometers may be added in whatever configuration is selected for a particular application.

Figure 4:
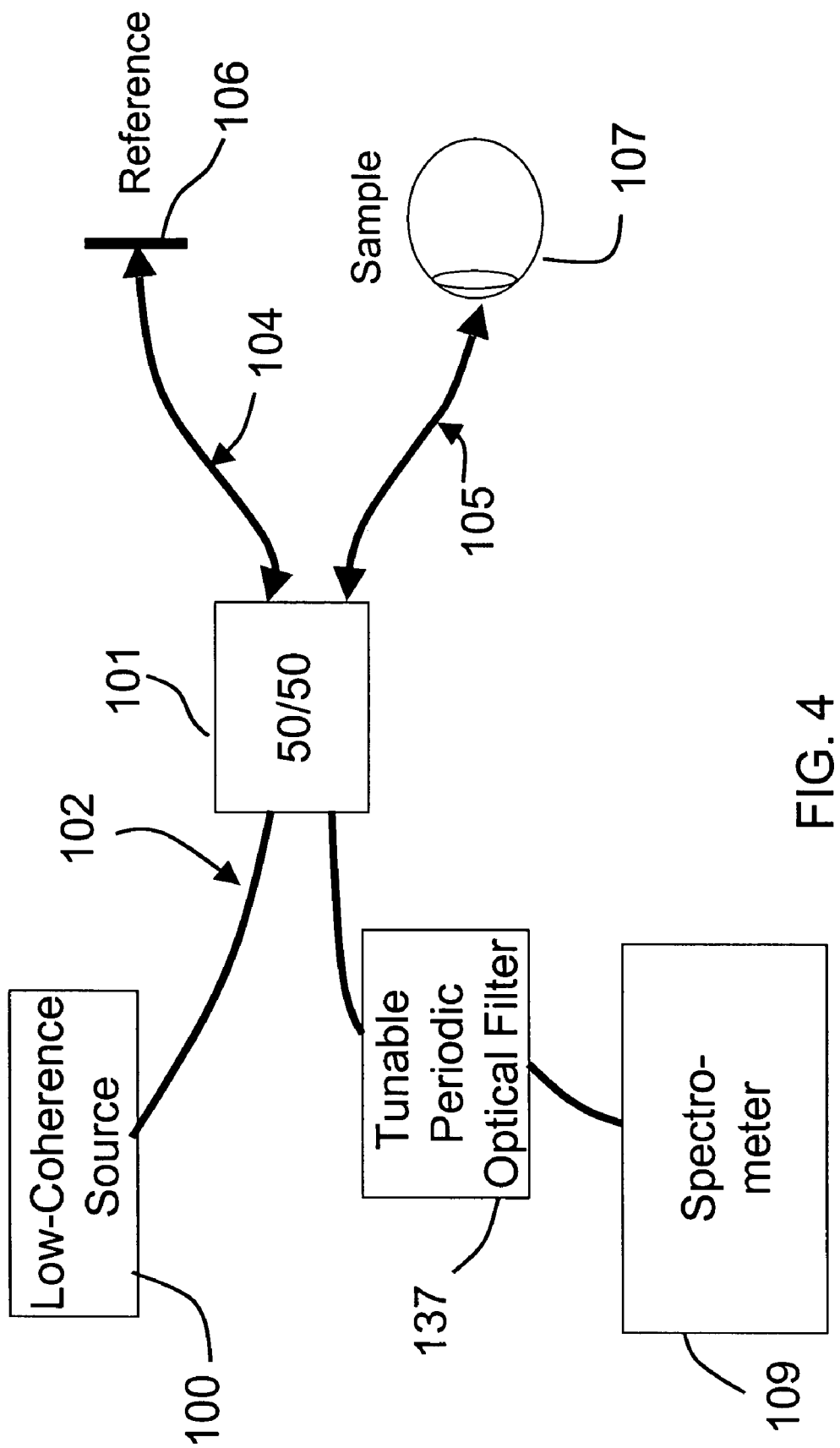
FIG. 4 is a schematic block diagram illustrating an optical engine (system) according to further embodiments of the present invention.

The embodiments of FIG. 4 are similar to those described with reference to FIG. 1 with the addition of a tunable POF 137. A tunable POF is one where the wavelength comb spectra on a particular output can be shifted in frequency by some control method. Multiple spectrometers could be used, but some embodiments only include one spectrometer 109 as shown in FIG. 4. The POF 137 may be an interleaver, a Fabry Perot cavity or other POF and may be tunable by various means including mechanical, electrical, or optical. In addition, to shifting the spectra, the free spectral range and the finesse of the cavity may be shifted in some embodiments.

In some embodiments the POF 137 is configured to tune fast enough to permit the spectrometer 109 to acquire spectra at a rate sufficient to support the desired image rate for the optical engine. In some embodiments, the tunable POF 137 can obtain the same results as the previously described combinations of POFs, optical switches and spectrometer, but may allow additional flexibility. Using a tunable POF generally involves a trade-off between the number of spectrometers and the time to acquire an image. In other words, the same result may be achieved with one spectrometer as with multiple spectrometers, but a longer time may be required to collect the full spectra. The embodiments of FIG. 4 may be easier to scale to higher POF finesse as only one spectrometer and no optical switches may be used. Real time control of the image acquisition rate versus image resolution tradeoff may also be provided.

By varying (increasing) the number of steps in the POF scan, the resolution can be increased and the fall off reduced. If a fast scan time is desired, the number of steps in the POF scan can be reduced. This approach can also be used in conjunction with the architectures described for the embodiments of FIGS. 1-10, to provide systems where one or more POFs are tunable and the number of spectrometers can be varied from 1 to many and the number of optical switches can be varied from 0 to many.

Figure 5A:
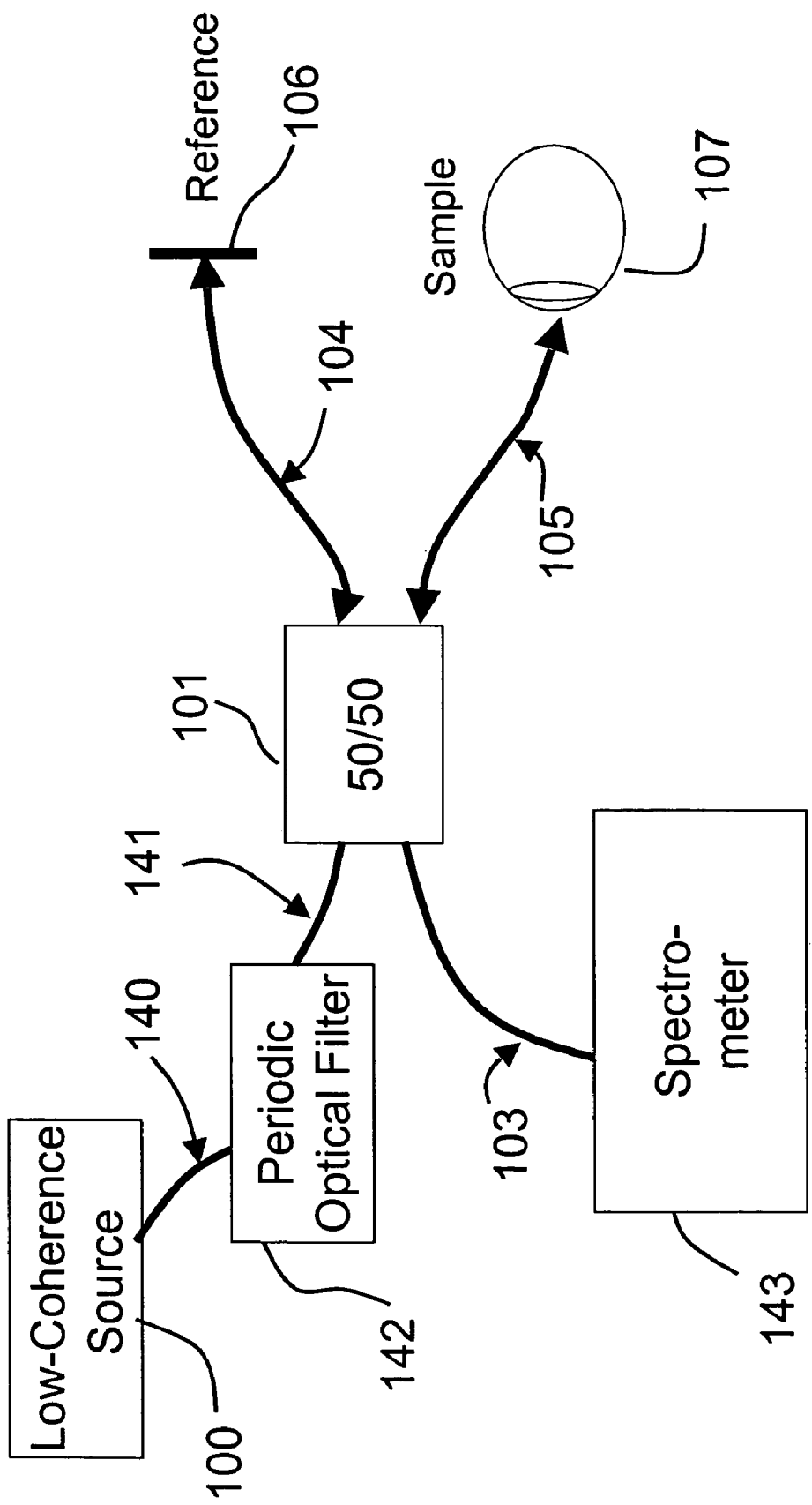
FIG. 5A is a schematic block diagram illustrating an optical engine (system) according to other embodiments of the present invention.

Referring now to the embodiments of FIG. 5A, a POF 142 is positioned in the source arm 140, 141 from the low-coherence source 100. This location may provide advantages similar to those described with reference to the embodiments of FIG. 4 but, as the POF 142 is prior to the splitter 101, the power incident on the reference arm 104 and sample arm 105 may be reduced. In the embodiments of FIG. 4, all wavelengths may be incident on the reference 106 and sample 107 at all times, even though only a fraction of the wavelength may pass through the POF 137 and enter the spectrometer 109 at any given time. In cases where there is a limitation on how much power should be incident on the sample 107, such as on the human eye for retinal scanning, power that does not pass through the POF 137 to the spectrometer 109 is wasted. For the embodiments of FIG. 5A, all power returning from the sample 107 through the splitter 101 and onto the spectrometer path (detector arm) 103 may enter the spectrometer 143. It will further be understood that the POF 142 of FIG. 5 may be a tunable or fixed POF.

Figure 5B:
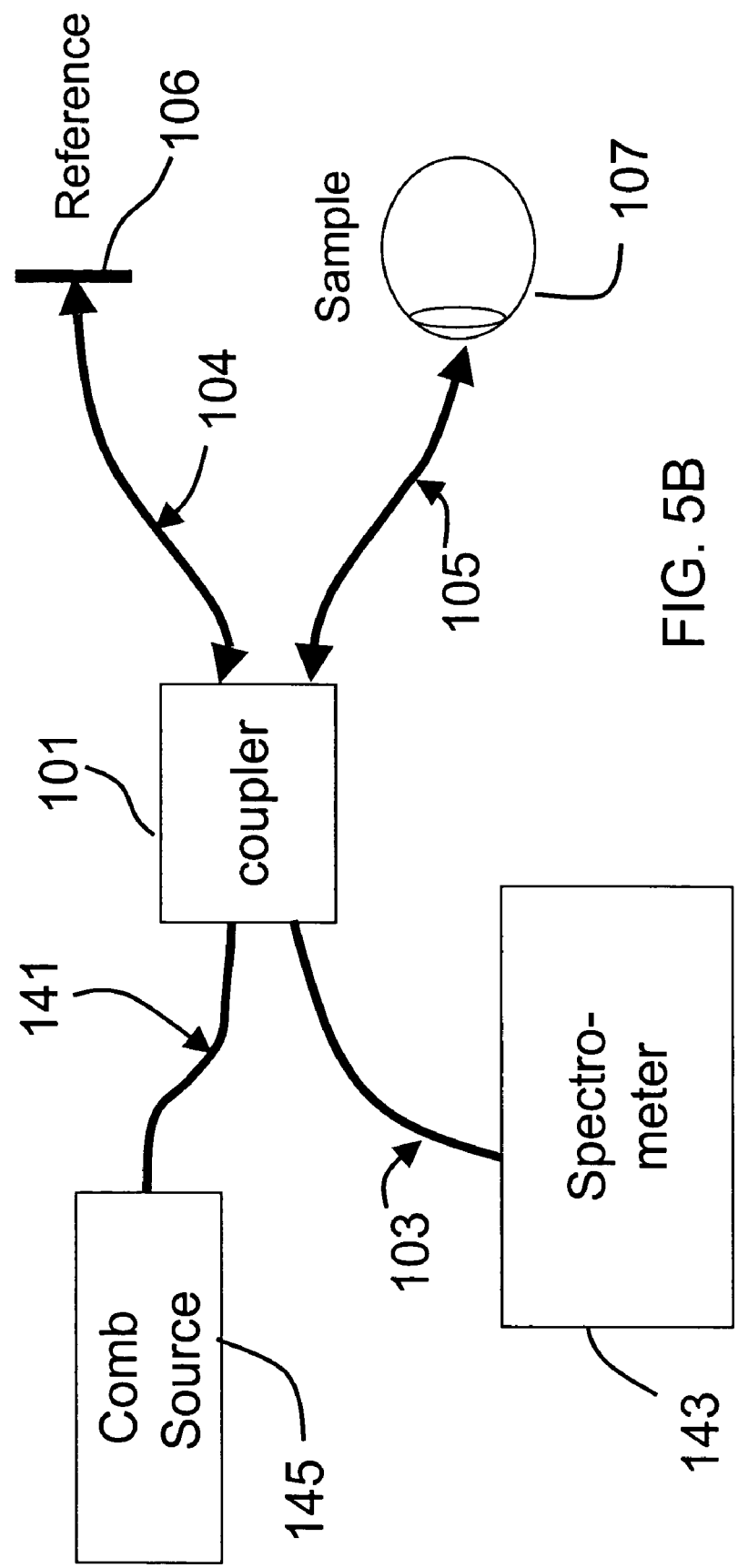
FIG. 5B is a schematic block diagram illustrating an optical engine (system) according to further embodiments of the present invention.

A variant of the embodiments of FIG. 5A is illustrated in FIG. 5B, where a comb source 145 takes the place of the low-coherence source 100 with the periodic optical filter 142 shown in FIG. 5A. The embodiments of FIG. 5B may provide substantially the same advantageous as the embodiments of FIG. 5A while using a different set of sources. The comb sources 145 provides a set of wavelengths 1 through N, where there is a spacing between each set of wavelengths and a linewidth associated with each wavelength. In some embodiments, the spacing between the wavelengths may be constant in wavelength, constant in wavenumber or frequency, chirped in wavelength or wavenumber, and/or may have some other spacing. There are a variety of ways to build comb sources, including, but not limited to, multi-mode or multi-line lasers, broadband sources with internal filtering and/or feedback, and/or other nonlinear optical devices.

Figure 6:
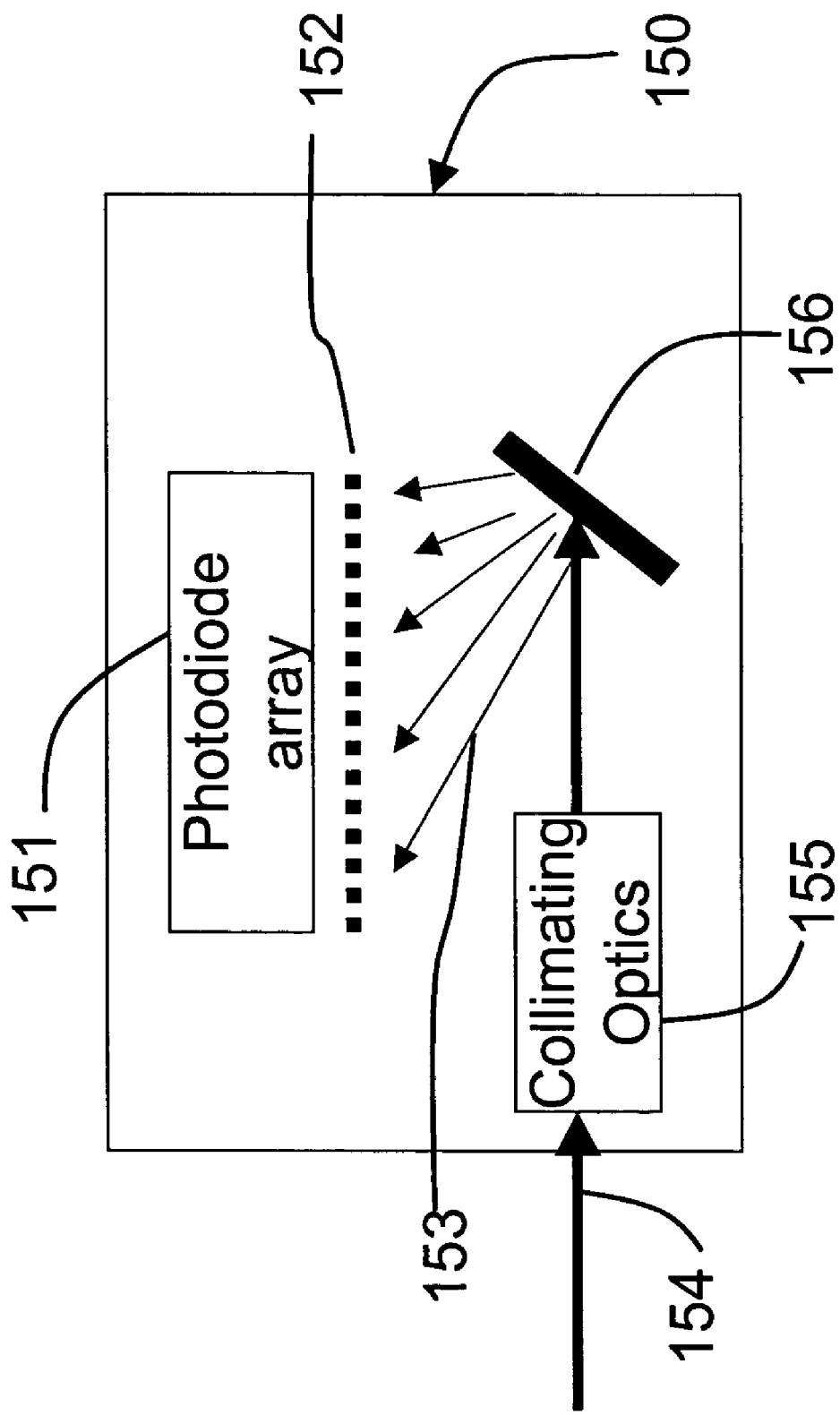
FIG. 6 is a schematic block diagram of an optical engine (system) according to some embodiments of the present invention.

Referring now to the embodiments of FIG. 6, the filtering and tunability described previously may be moved inside a spectrometer 150. This may provide the same functionality as, for example, the embodiments of FIG. 3, but may do so while reducing the number of devices in and the cost of the OCT imaging system. The spectrometer 150 may include an input source 154, some input or collimating optics 155, a dispersive device 156 and a photodiode array 151.

As shown in the embodiments of FIG. 6, filtering is added to the spectrometer 150 in the form of a spatial mask 152, which restricts the light 153 falling on the pixels of the photodiode array 151. The mask 152 can be configured so that it is periodic in wavelength and/or chirped so it is periodic in frequency. The size of the holes in the spatial mask 152 can be specified to control the percentage of each pixel that is lit. This may be used to control the rate of fall off of the image.

Furthermore, the spectrometer of the embodiments of FIG. 6 can also be implemented as a tunable spectrometer, for example, by moving the collimating optics 155, the diffractive element 156, the spatial mask 152, and/or the photodiode 151. Other tunable embodiments may be provided including adding additional optics, such as a movable mirrors or prisms, and/or varying the effective index of refraction in the spectrometer 150 by changing the temperature and/or pressure of the gas inside the spectrometer.

Figure 7:
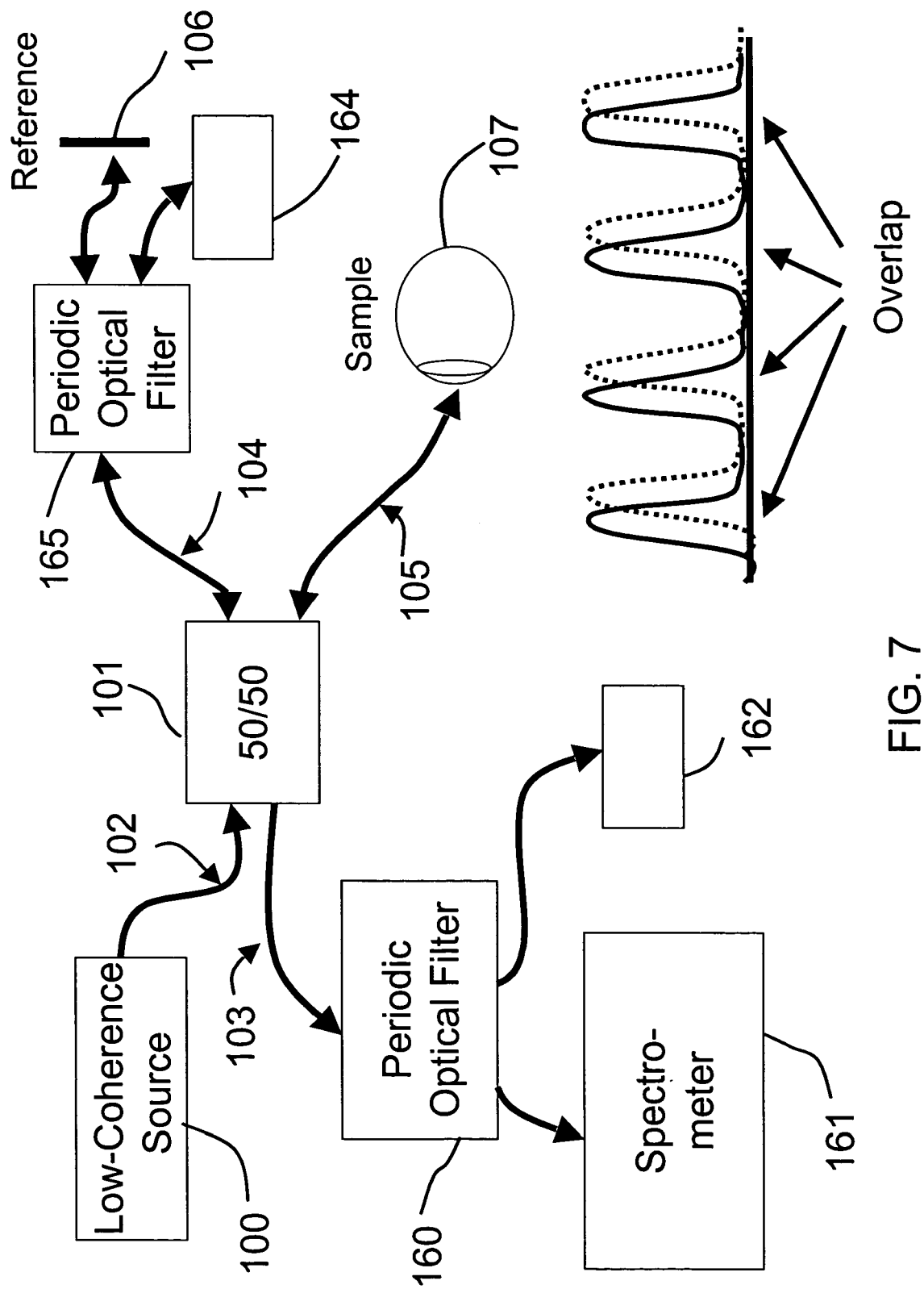
FIG. 7 is a schematic block diagram of an optical engine (system) according to further embodiments of the present invention.

Further embodiments are illustrated in the schematic block diagram of FIG. 7. As shown in the embodiments of FIG. 7, at least two POFs 160 and 165 are used in different arms 103 and 104 coupled to the splitter 101. At least one of the POFs 165 is in either the reference arm 104 (as shown in FIG. 7) or the sample arm 105 of the interferometer (optical engine) and the second POF 160 may be in any of the other three arms 102, 103 and 105 that is not occupied by the POF 165. By offsetting the two POF's 160 and 165 relative to each other, the effective bandwidth of the comb can be reduced below the bandwidth of either POF 160 and 165. As an example, two interleavers (POFs) with the same FSR and finessees of 2 could be offset by one quarter of the FSR to achieve an effective filter width that is one half the width of either interleaver. This may result where interference at the spectrometer 161 only occurs for wavelengths that are present in both the reference arm 104 and the sample arm 105 of the interferometer.

By combining the configuration of FIG. 7 with the use of tunable POFs, a device may be provided where the effective finesse is readily controlled. While the embodiments of FIG. 9 discussed below generally address this feature, it may be more difficult to build a POF where the finesse is adjustable than to build a POF where the output comb is tunable in wavelength. By tuning the output comb of both POFs 165 and 160 in the embodiments of FIG. 7, the location and width in wavelength of the light on each photodiode of the spectrometer 161 may be controlled. This may permit control of the rate of fall off of the image and the image depth. The tradeoff may be in the amount of power on the photodiodes in the spectrometer 161 and the time required to build up sufficient data for an image.

Also schematically shown in the embodiments of FIG. 7 are optional additional devices 162 and 164 that may be connected to additional ports of the POFs 160, 165, respectively. These additional ports may not be connected to anything but information is available in the light on these additional ports. As such, for example, an additional spectrometer 162 could be coupled to the POF 160 and a power or other spectrum monitor device 164 could be coupled to the POF 165.

Also shown in FIG. 7 are a dotted line graph and a solid line graph. The solid line represents a passband shape for the first POF 165 and the dotted line represents the passband shape for the second POF 160 according to some embodiments. The combined passband (or the overlap) may give narrower peaks then either POF by itself. Such narrower lines may be desirable, however, the cost and complexity of a POF generally increases with the narrowness of the lines. Thus, a two POF design may provide narrower lines at a lower cost. Also if one or both POFs are tunable, then in some embodiments the overlap can be adjusted in a manner determined based on the particular application of the optical engine.

Figure 8:
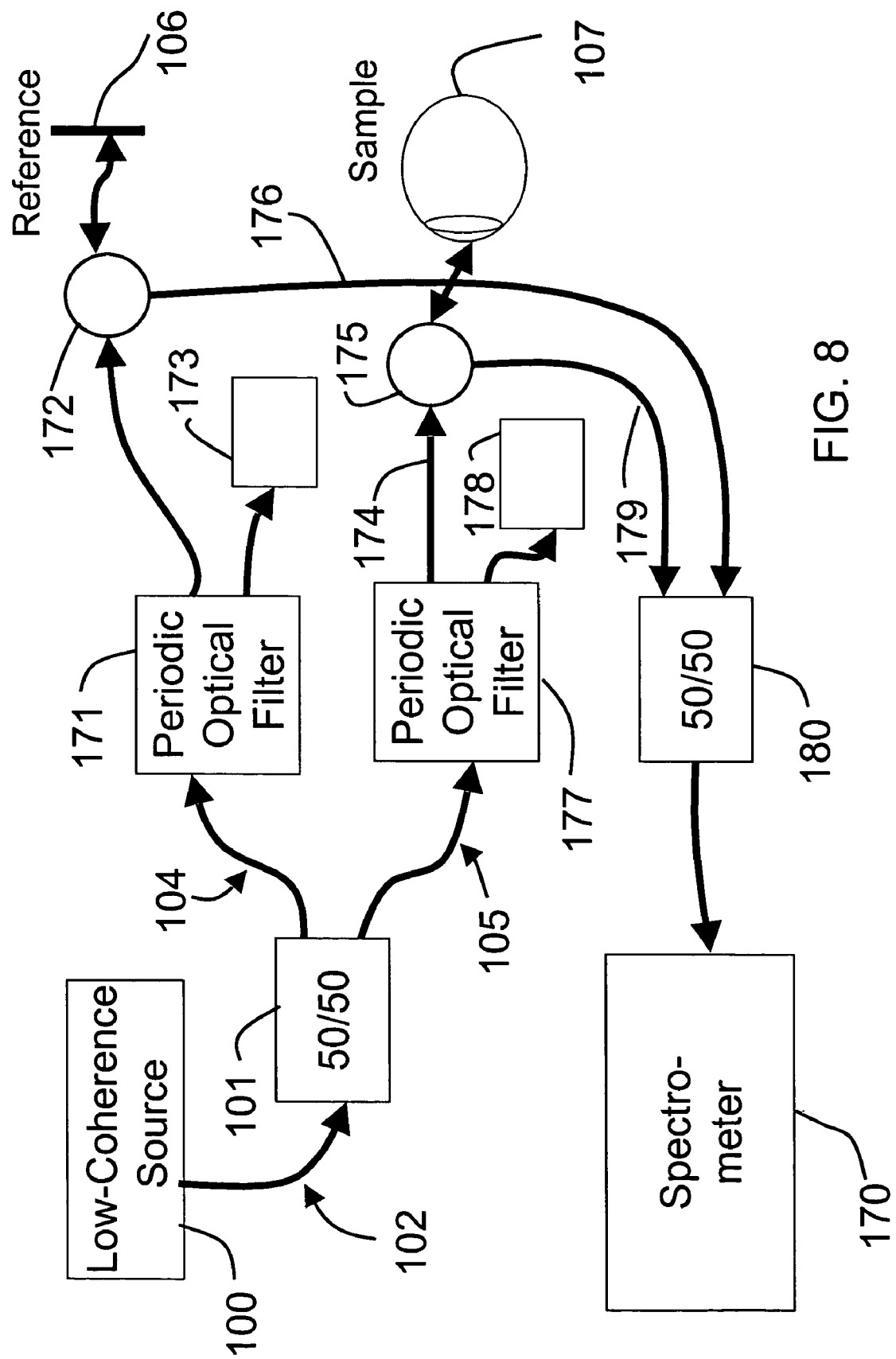
FIG. 8 is a schematic block diagram of an optical engine (system) according to other embodiments of the present invention.

Further embodiments are illustrated in the schematic block diagram of FIG. 8. In the embodiments of FIG. 8, only one pass of each POF 171 and 177 is used. As shown in FIG. 8, the POFs 171 and 177 are used in conjunction with circulators 172 and 175 so that light from the low-coherence source 100 through the first coupler splitter 101 passes through the POFs 171 and 177 and light returning from the reference 106 and the sample 107 does not pass through POFs 171 and 177 again on the return, but is diverted by the circulators 172 and 175 to the second coupler splitter 180 on optical connections 176 and 179 and, hence, to the spectrometer 170. This may be desirable if the POFs 171 and 177 have high insertion loss, particularly in comparison to the circulators 172 and 175. Various aspects of tenability over a range of wavelengths present in the embodiments of FIG. 7 may also be used in the embodiments of FIG. 8.

Also schematically shown in the embodiments of FIG. 8 are optional additional devices 173 and 178 that may be connected to additional ports of the POFs 171 and 177, respectively. These additional ports may not be connected to anything, but information is available in the light on these additional ports.

Figure 9:
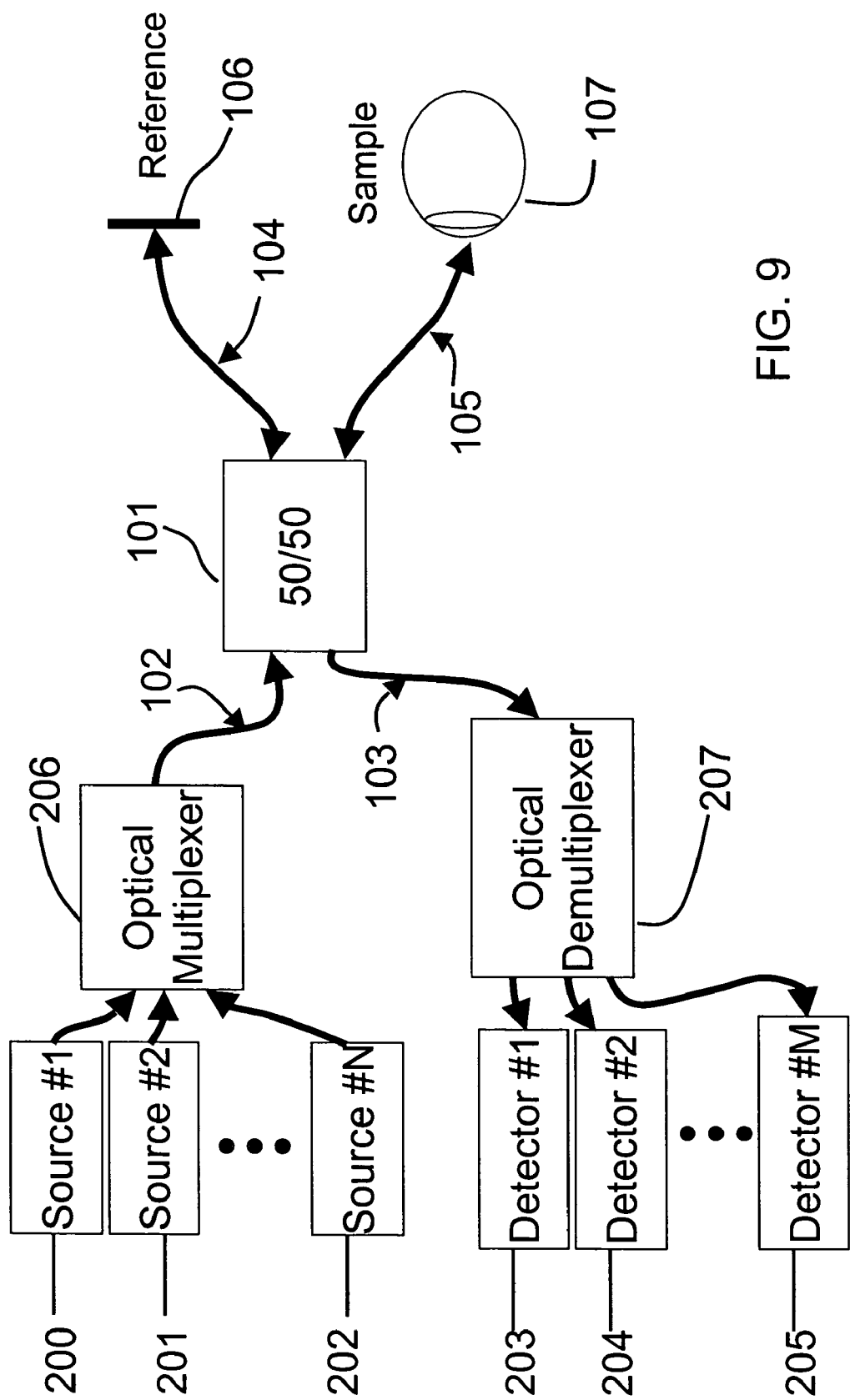
FIG. 9 is a schematic block diagram of an optical engine (system) according to further embodiments of the present invention.

The embodiments of FIG. 9 include one or more optical multiplexers and demultiplexers as the optical filters. Multiple sources 200, 201 and 202 are multiplexed by the optical multiplexer 206 onto a single fiber in the source arm 102 of the optical engine (interferometer) to provide a super-source and then demultiplexed by the optical demultiplexer 207 in the detector arm 103 onto multiple detectors 203, 204 and 205. The multiplexer 206 could be an arrayed waveguide (AWG), concatenated thin film filters, fiber Bragg gratings, power couplers, and/or the like. The demultiplexer 207, in some embodiments, has some wavelength discrimination capability rather than using a simple splitter.

The sources may be tunable lasers with detectors (as shown in FIG. 9) and/or super luminescent diode sources combined with spectrometers on the detection side. The number of sources (either swept or broadband) and detectors (individual or in spectrometers) does not need to match although, in some embodiments, any detector, whether individual, in an array and/or part of a spectrometer, sees light only from either one source or only at one wavelength.

As noted previously, the effective wavelength spread seen by a detector may determine the rate of image falloff. The effective wavelength spread may be set by the source (narrowband swept source laser) or by filtering in the system. With this approach, any of the previous POF configurations may also be used. POFs may be added in the source arm 102, the reference arm 104, the sample arm 105, the detector arm 103, or any combination thereof. Any and all of the POFs could be tunable as well as the sources given by 200, 201 and 202 and the detectors 203, 204 and 205.

Figure 10:
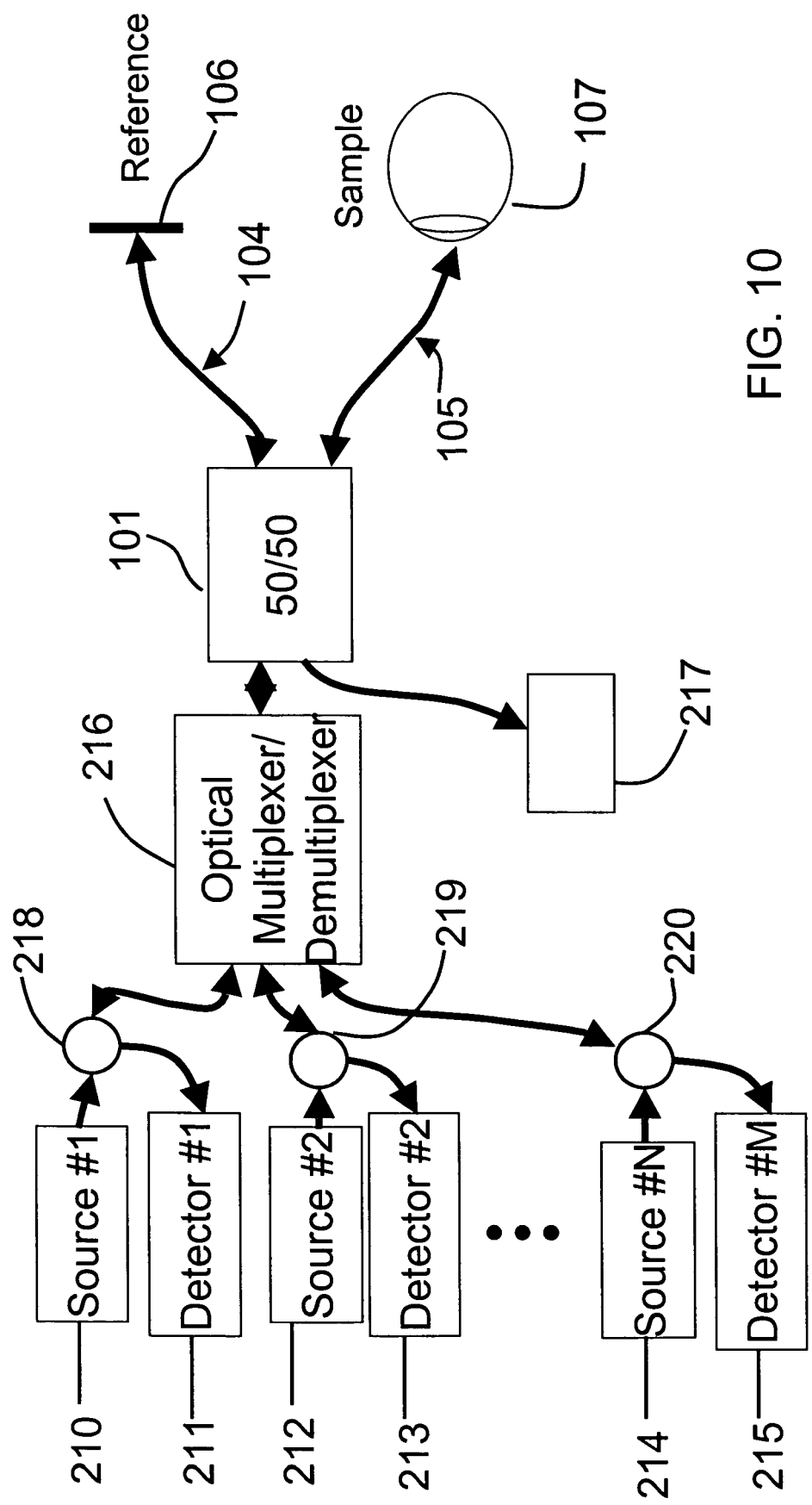
FIG. 10 is a schematic block diagram of an optical engine (system) according to further embodiments of the present invention.

As illustrated in FIG. 10, further embodiments are similar to the description of the embodiments of FIG. 9 above, but with the use of a set of circulators 218, 219 and 220 and an optical multiplexer/demultiplexer 216 instead of the optical multiplexer and demultiplexer 206 and 207. Each circulator 218, 219 and 220 is coupled to an associated source 210, 212 and 214 and an associated detector 211, 213 and 215. This difference may provide flexibility in design selection based on the cost of circulators versus optical multiplexers or demultiplexers and the potential requirements that the multiplexer and demultiplexer be identical.

Also schematically shown in the embodiments of FIG. 10 is an optional additional device 217 that may be connected to an additional port of the splitter/coupler 101. This additional port may not be connected to anything but information is available in the light on this additional port.

Figure 11:
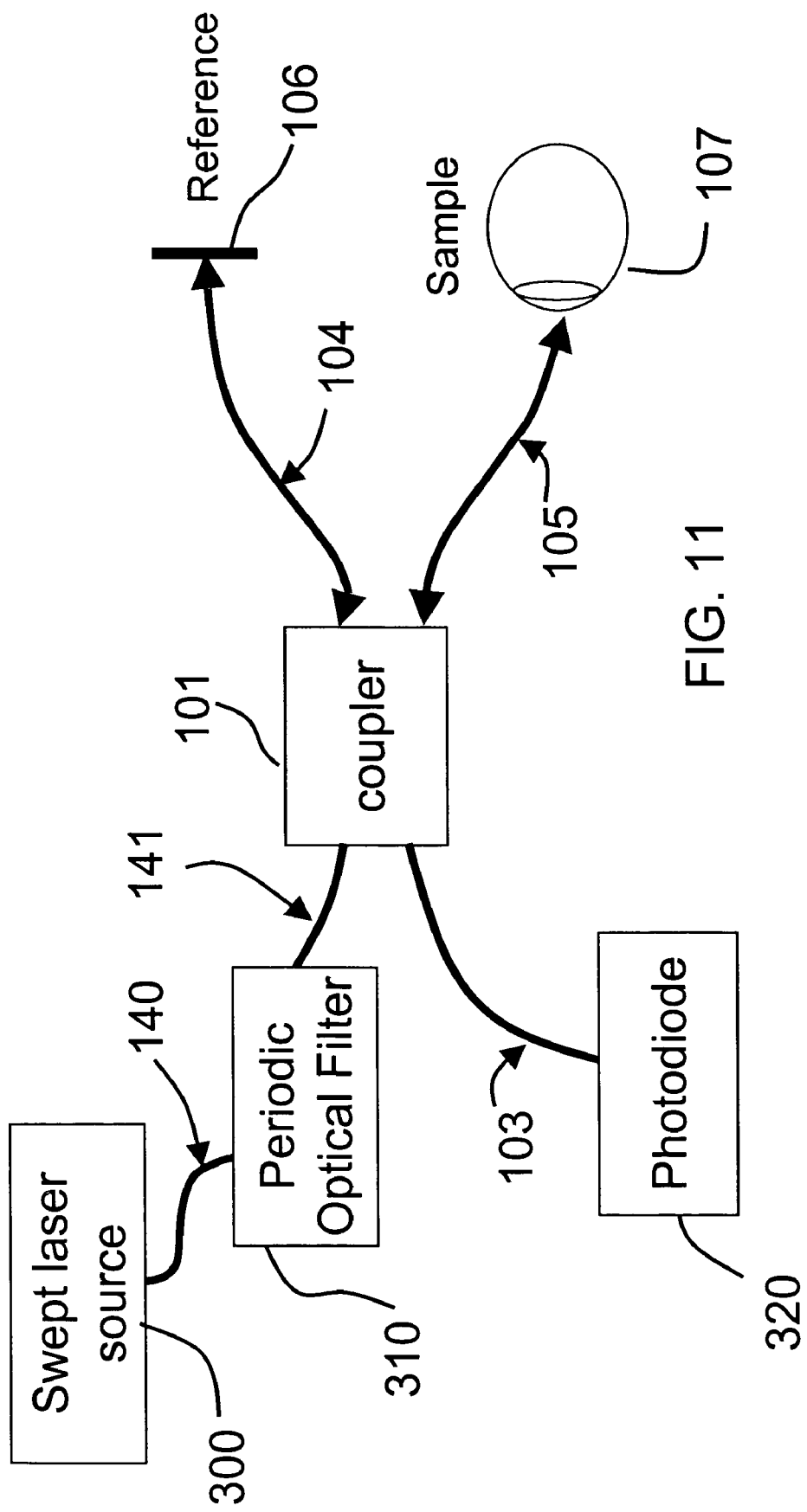
FIG. 11 is a schematic block diagram of an optical engine (system) according to further embodiments of the present invention.

Further embodiments are shown in FIG. 11, which embodiments are similar to the embodiments of FIG. 5A, but a swept laser source 300 is used with one or more photodiodes 320 instead of using a broadband or low coherence source 100 with a spectrometer 143 as shown in FIG. 5A. The embodiments of FIG. 11 may provide substantially the same advantages as the embodiments of FIG. 5A, such as controlling the effective linewidth and minimizing optical power on the sample while providing a new set of sources that can be used in the system implementation. By using the POF 310, the linewidth of the laser can be broadened to approximately the free spectral range (spacing) (FSR) of the POF 310 while the system still may have the effective linewidth characteristics of the linewidth of the POF 310.

Figure 12:
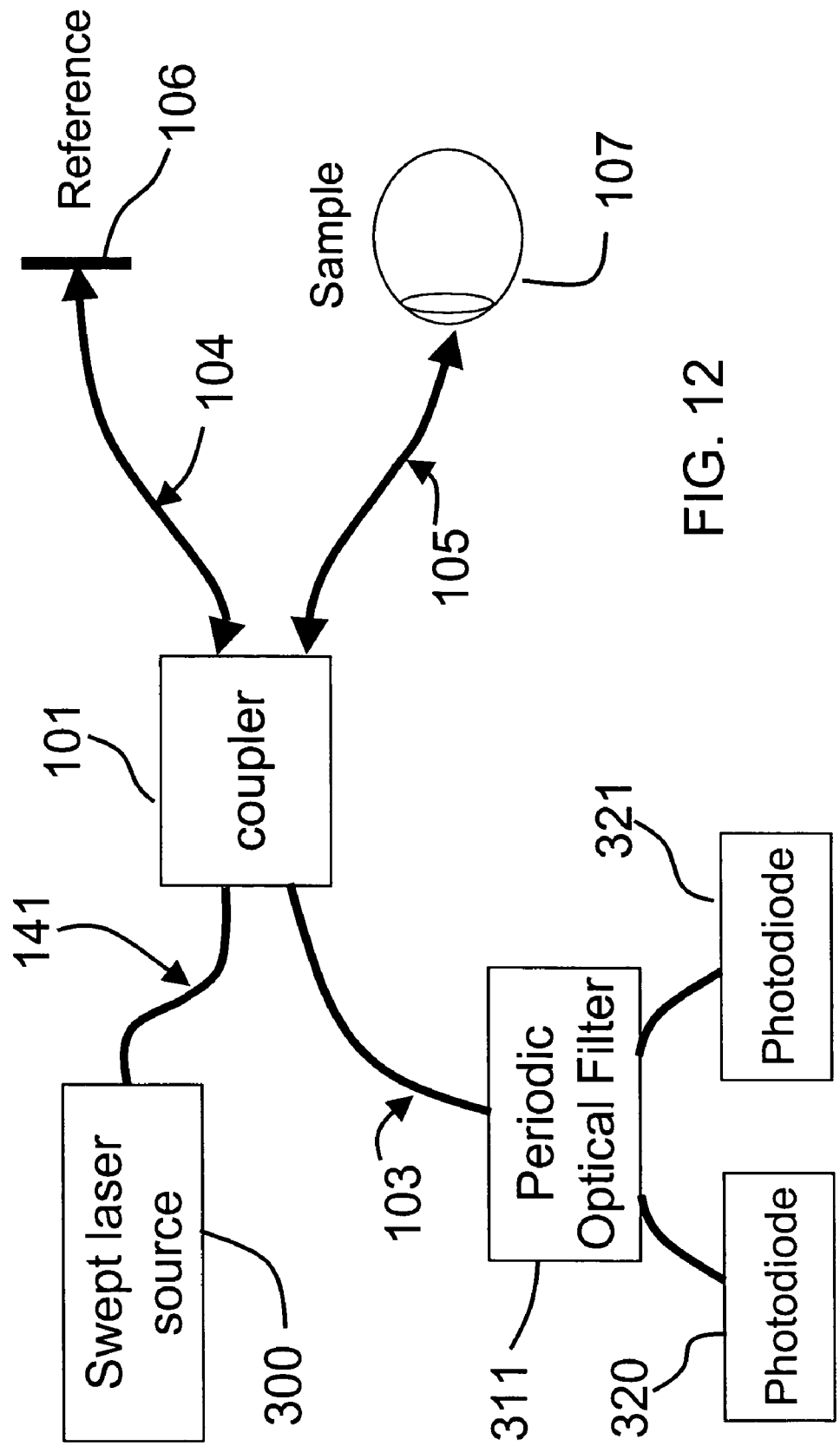
FIG. 12 is a schematic block diagram of an optical engine (system) according to further embodiments of the present invention.

The embodiments of FIG. 12 are similar to the embodiments of FIG. 11. However, FIG. 12 uses a swept laser source 300, but with a POF 311 in the detector arm 103 rather than in the source arm 141. The POF 311 may be connected to one or more photodiodes 320, 321. The embodiments of FIG. 12 may have substantially the same advantageous as the embodiments of FIG. 11 in that the effective linewidth of the source can be controlled while also offering the ability to increase the imaging depth by acquiring light from more than one port of the POF 311.

Figure 13:
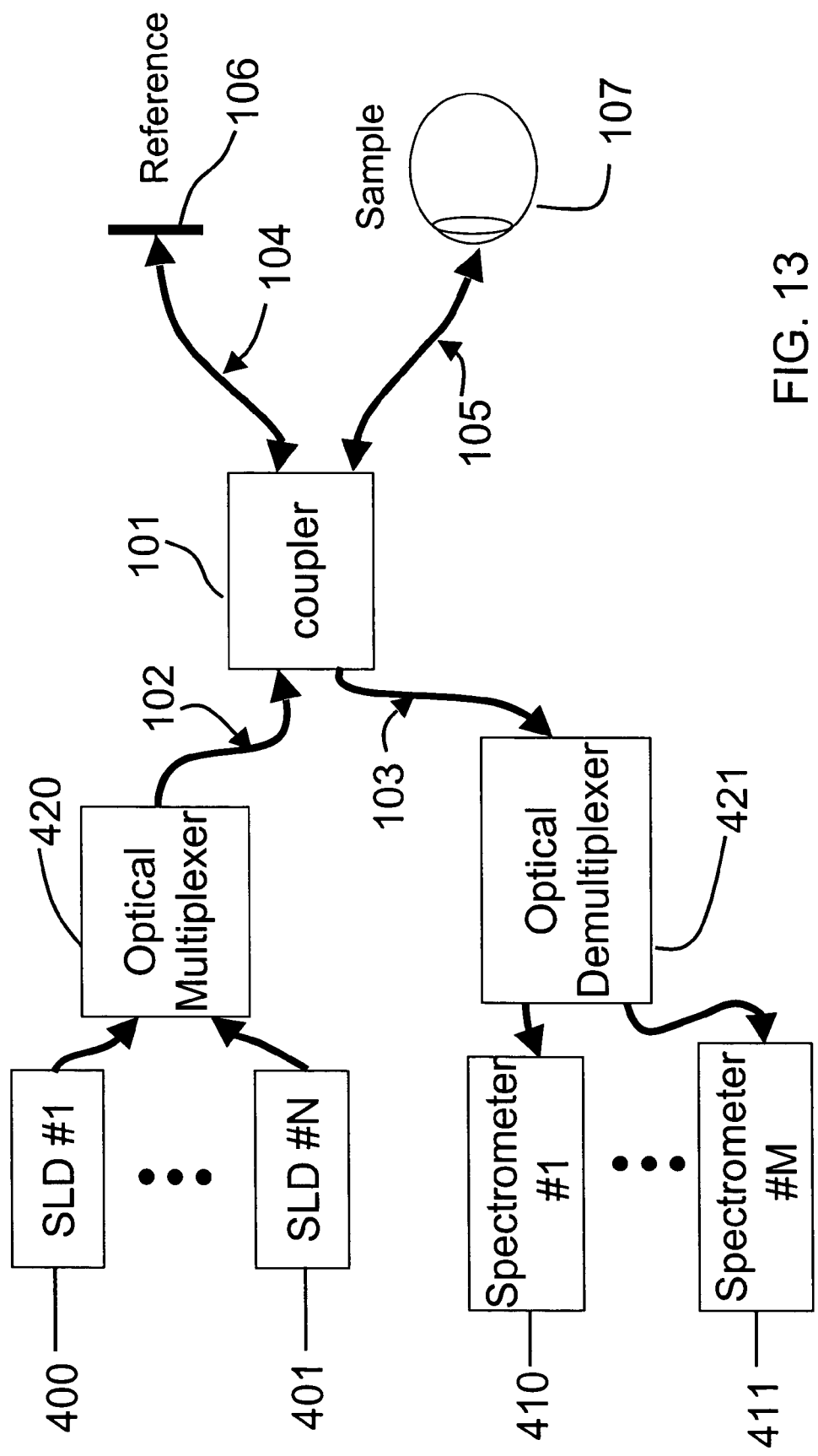
FIG. 13 is a schematic block diagram of an optical engine (system) according to further embodiments of the present invention.

FIG. 13 illustrates further embodiments where multiple SLDs 400, 401 are multiplexed together by a multiplexer 420 to create a source which may have enhanced characteristics, for example, a broader total bandwidth. Similarly, one or more spectrometers 410, 411 may be used in the detector arm connected together by a demultiplexer 421. In the embodiments of FIG. 13, the multiplexer 420 and demultiplexer 421 may combine and separate the light from various ports based on wavelength and/or may simply be couplers that mix the light together based on power and/or other devices for combining and separating light. The multiplexer 420 and the demultiplexer 421 may also have properties of a POF where an effective linewidth is modified for one or more of the detector(s) in the spectrometer(s) 410, 411. In some embodiments, there may be one or more separate POF(s) in the source arm 102 and/or the reference arm 104 and/or the sample arm 105 and/or the detector arm 103.

Figure 14:
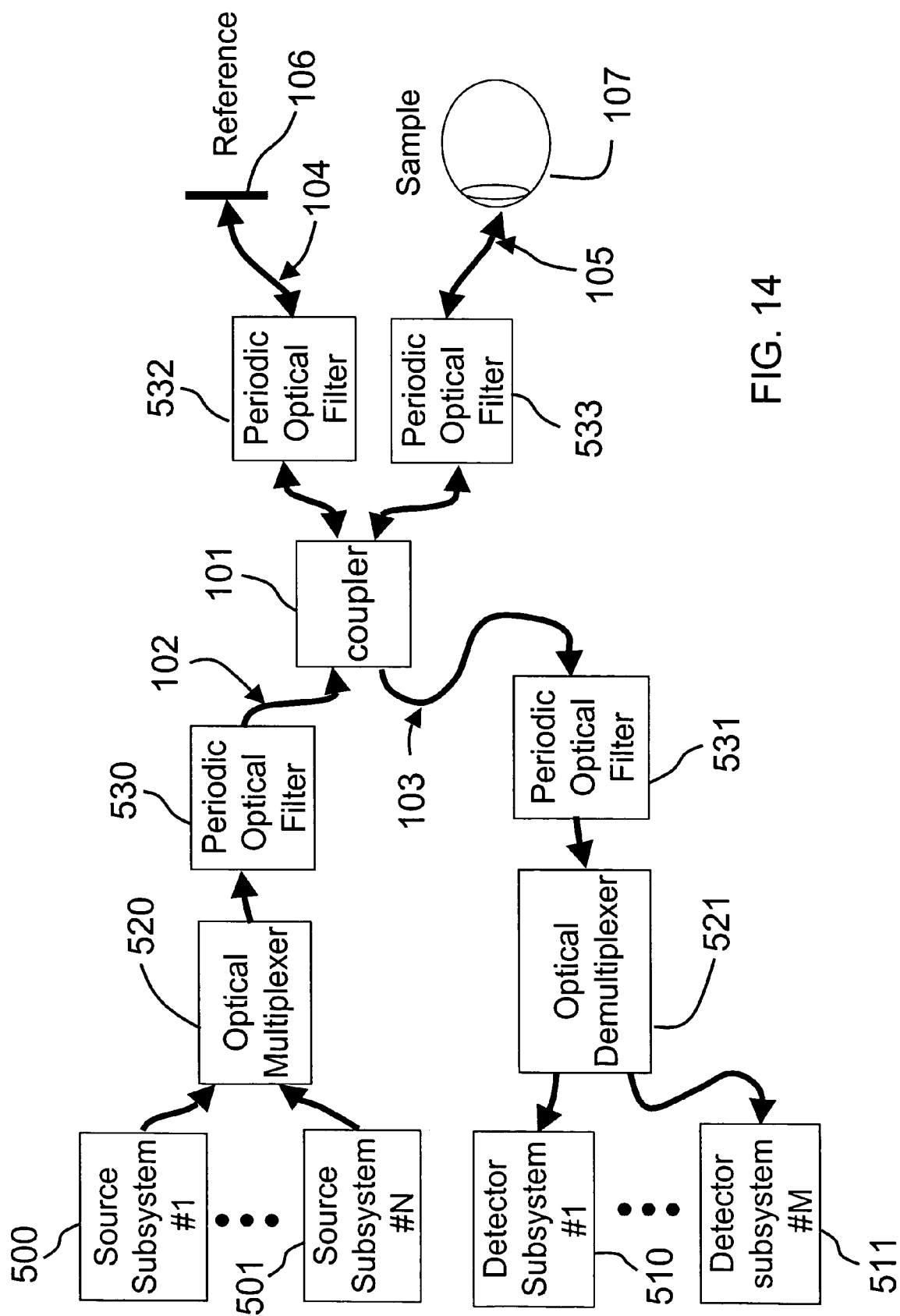
FIG. 14 is a schematic block diagram of an optical engine (system) according to further embodiments of the present invention.

Yet further embodiments of the present invention are illustrated in FIG. 14, where one or more source subsystems 500,501 are connected to a source arm 102, which may or may not include optical multiplexer(s) 520 and POF(s) 530. The reference arm 104 and the sample arm 105 may or may not include POF(s) 532 and 533. The detector arm 103 is illustrated as including one or more detector subsystem(s) 510, 511 and may or may not also include optical demultiplexer(s) 521 and/or POF(s) 531. The source subsystems 500, 501 generate light and may include SLD's, swept laser sources, comb sources, other light sources, and/or a mixture of various light sources. Likewise the detector subsystems 510, 511 detect light and may include single photodiodes, photodiode(s) with filters, spectrometers, other light detection devices and/or mixtures of various detector implementations. In some embodiments, a system design requirement is that there are acquisitions from one or more detectors that can be mapped relative to each other in wavelength (or wavenumber). This mapping may be some combination of time and wavelength, such as reading a line of data from a spectrometer or a time series of data from a detector, but can be any combination or implementation such that there is a defined mapping and the system can sample light from know wavelengths or wavelength spacings at know times or time spacings.

In some embodiments of the present invention, optical engines (systems) include an optical source, a plurality of optical detectors, a plurality of interferometers and two or more optical filters. One or more of the optical filters may be POFs that are periodic in frequency. POF(s) may be in the spectrometer arm and two or more spectrometers may be included. POF(s) may be in the spectrometer arm and one or more optical switching element(s) and one or more spectrometers may be included. POF(s) may be in the source arm. One or more of the POFs may be tunable.

In some embodiments of the present invention, one or more POFs are in the reference arm and one or more POFs are in the sample arm and circulators are between the POFs and reference or sample. In such embodiments, light only traverses the POF once and goes to the spectrometer via the circulator and another combiner. The spectrometer may be a tunable spectrometer.

In some embodiments, the POF is provided as a sub-pixel mask that may be used in combination with a tunable spectrometer. The spectrometer may have chirped pixels. The pixels may be chirped by having an increasing width. The pixels may be chirped by having a constant width and an increasing gap. Two or more POFs may be included that may be offset in frequency. One or more POF(s) may be in the reference arm and one or more POF(s) may be in the sample arm. One or more of the POFs may be tunable.

In some embodiments, one POF is in the sample arm and one POF is in the spectrometer arm. One POF may be in the reference arm and one POF may be in spectrometer arm. One or more of the POFs may be tunable.

In some embodiments of the present invention, optical engines (systems) include two or more optical sources, a plurality of muxing devices for the sources, a plurality of optical detectors, a plurality of interferometers, and a plurality of optical filters. The sources may be lasers and one or more of the lasers may be tunable. The muxing devices may be configured to provide power muxing, polarization muxing and/or wavelength dependent muxing.

In some embodiments, filters are in the detector arm. The filters may include arrayed waveguides (AWGs), thin film filters, echelon gratings and/or Fiber Bragg Gratings. The sources may be superluminescent diodes (SLDs) that may be tunable.

It will be understood that, with a FD-OCT system, the detector system generally knows what wavelength spacings it is interrogating so that it can generate a set of intensity values as a function of wavelength. This information may then be fed into an FFT to generate the depth image. As such, the fall-off in such imaging systems is generally determined by the effective linewidth (bandwidth) of the light seen by the detector system when an amplitude measurement is taken. Previous approaches to obtain a desired effective linewidth included using a swept source where the linewidth of the source becomes the effective linewidth and using a spectrometer where the linewidth viewed by a single detector in the array becomes the effective linewidth. As described above, various embodiments of the present invention provide a variety of different approaches to set the effective linewidth. Some embodiments of the present invention may provide a narrower (less fall-off) effective linewidth than the previously known approaches.

In addition, in some embodiments, there may also be other advantages in using combinations of sources and detectors to create a source subsystem and a detector subsystem that may have better performance, including: (1) higher output power, (2) faster sweep rates, (3) larger total bandwidths, and/or (4) cheaper construction costs. As such, some embodiments of the present invention may provide better performance relative to the issue of fall-off while allowing commercial building of such FD-OCT systems. As described above some embodiments involve the use of optical filters and/or combinations of sources and/or detectors to provide imaging systems that may include a source subsystem, a detector subsystem, a reference arm, and a sample arm connected to an interferometer where the design of the source subsystem and the detector subsystem produce a narrower effective linewidth than previously known approaches.

In some embodiments, a source selection rather than optical transmission path design may provide such effective linewidth narrowing, for example, through the use of a comb source. A comb source with a spectrometer may provide a solid state system with no sweeping while, nonetheless, providing a better falloff as the linewidth of the comb source may be used to set the fall-off instead of or in addition to the linewidth of a pixel in the spectrometer.

In the drawings and specification, there have been disclosed typical illustrative embodiments of the invention and, although specific terms are employed, they are used in a generic and descriptive sense only and not for purposes of limitation, the scope of the invention being set forth in the following claims.

That which is claimed is:

1. A frequency domain optical coherence imaging system, comprising:
   an optical source, wherein the optical source comprises a broadband source;
   an optical detector; and
   an optical transmission path between the optical source and the optical detector that reduces an effective linewidth of the imaging system, wherein the optical transmission path includes:
   an optical splitter having a first side including a port coupled to a source arm and a port coupled to a detector arm and a second side having a port coupled to a reference arm and a port coupled to a sample arm and a periodic optical filter;
   wherein the frequency domain optical coherence imaging system further comprises:
   the periodic optical filter positioned in the detector arm between the optical splitter and the optical detector, the optical detector comprising a first spectrometer and a second spectrometer and wherein the periodic optical filter has a first output coupled to the first spectrometer and a second output coupled to the second spectrometer, the periodic optical filter comprising an interleaver having a finesse of two;
   the periodic optical filter positioned in the detector arm between the optical splitter and the optical detector, the optical detector comprising a first spectrometer and a second spectrometer and wherein the periodic optical filter has a first output coupled to the first spectrometer and a second output coupled to the second spectrometer, the periodic optical filter comprising an interleaver having a finesse of greater than two;
   the periodic optical filter positioned in the detector arm between the optical splitter and the optical detector, the optical detector comprising a first spectrometer and a second spectrometer and wherein the periodic optical filter has a first output coupled to the first spectrometer and a second output coupled to the second spectrometer, the periodic optical filter having a free spectral range that substantially matches a pixel spacing of the first and second spectrometer;
   the periodic optical filter positioned in the detector arm between the optical splitter and the optical detector, wherein the optical detector comprises a spectrometer and wherein the frequency domain optical coherence imaging system further comprises an optical switching device in the detector arm that selectively couples a plurality of outputs of the periodic optical filter to the spectrometer;
   the periodic optical filter positioned in the detector arm between the optical splitter and the optical detector wherein the periodic optical filter comprises a cascaded plurality of optical filters and wherein the optical detector comprises a first and a second spectrometer and wherein the cascaded periodic optical filters have a first output coupled to the first spectrometer and a second output connected to the second spectrometer, the first output comprising a first set of outputs from one of the cascaded periodic optical filters and the second output comprising a second set of outputs from another of the cascaded periodic optical filters and wherein the frequency domain optical coherence imaging system further comprises a first optical switching device coupling the first set of outputs to the first spectrometer and a second optical switching device coupling the second set of outputs to the second spectrometer; and/or
   the periodic optical filter comprising a first periodic optical filter and wherein the system further comprises a second periodic optical filter and wherein the first periodic optical filter is positioned in the reference arm or the sample arm and the second periodic optical filter is positioned in a different arm of the system, wherein the first and second periodic optical filters are interleavers having a substantially same free spectral range (FSR) and a finesse of at least two and wherein the first and second periodic optical filters are offset by about one quarter of the FSR.

2. The system of claim 1, wherein the broadband source comprises a swept laser source.

3. The system of claim 1, wherein the optical detector comprises a plurality of optical detectors and wherein the optical transmission path includes a spatial mask positioned proximate the optical detectors.

4. The system of claim 3, wherein the plurality of optical detectors comprises a spectrometer and wherein the spatial mask is positioned in the spectrometer.

5. The system of claim 4, wherein the spectrometer comprises a tunable spectrometer.

6. The system of claim 1, wherein the optical detector comprises the first spectrometer and the second spectrometer and wherein the periodic optical filter has the first output coupled to the first spectrometer and the second output coupled to the second spectrometer.

7. The system of claim 6, wherein the periodic optical filter comprises the interleaver having a finesse of two.

8. The system of claim 6, wherein the periodic optical filter comprises the interleaver having a finesse of greater than two.

9. The system of claim 6, wherein the periodic optical filter has the free spectral range that substantially matches the pixel spacing of the first and second spectrometer.

10. The system of claim 6, wherein the optical detector comprises the spectrometer and wherein the system further comprises the optical switching device in the detector arm that selectively couples the plurality of outputs of the periodic optical filter to the spectrometer.

11. The system of claim 1, wherein the periodic optical filter is positioned in the detector arm between the optical splitter and the optical detector, wherein the optical detector comprises a spectrometer and wherein the frequency domain optical coherence imaging system further comprises the optical switching device in the detector arm that selectively couples the plurality of outputs of the periodic optical filter to the spectrometer and wherein the optical detector comprises the spectrometer and wherein the system further comprises the optical switching device in the detector arm that selectively couples the plurality of outputs of the periodic optical filter to the spectrometer and wherein the periodic optical filter comprises an interleaver having a finesse of two and wherein the plurality of outputs of the periodic filter comprise a first comb output and a second comb output, each having substantially equal peak widths and wherein the second comb output is offset from the first comb output by about half of a free spectral range of the periodic optical filter.

12. The system of claim 1, wherein the first output comprises the first set of outputs from one of the cascaded periodic optical filters and the second output comprises the second set of outputs from another of the cascaded periodic optical filters and wherein the system further comprises:
the first optical switching device coupling the first set of outputs to the first spectrometer; and
the second optical switching device coupling the second set of outputs to the second spectrometer.

13. The system of claim 12 wherein the cascaded periodic filters are configured to generate the first and second set of outputs by splitting an optical signal input into a plurality of combs that are periodic and offset from each other.

14. The system of claim 13, wherein the first and second spectrometer have a pixel spacing substantially equal to a largest free spectral range of the cascaded periodic optical filters.

15. The system of claim 14, wherein the cascaded periodic optical filters include at least one output not coupled to the first or the second spectrometer and wherein an image falloff of the system is determined based on a filter width of a narrowest of the periodic optical filters and wherein a falloff of the system is determined based on a minimum optical interval between pixels of the optical detector.

16. The system of claim 1, wherein the periodic optical filter comprises a tunable periodic optical filter having a selectable output wavelength comb spectra.

17. The system of claim 16, wherein the tunable periodic optical filter has a selectable free spectral range and/or finesse.

18. The system of claim 16, wherein the tunable periodic optical filter has a tuning rate selected based on a desired image rate for the system.

19. The system of claim 16, wherein the tunable periodic optical filter has a number of steps in a scan selected to provide a desired resolution and/or falloff.

20. The system of claim 1, wherein the periodic optical filter is positioned in the source arm between the optical splitter and the optical source.

21. The system of claim 20, wherein the periodic optical filter comprises a cascaded plurality of optical filters.

22. The system of claim 20, wherein the periodic optical filter comprises a tunable periodic optical filter having a selectable output wavelength comb spectra.

23. The system of claim 22, wherein the tunable periodic optical filter has a selectable free spectral range and/or finesse.

24. The system of claim 1, wherein the first and second periodic optical filters are the interleavers having the substantially same free spectral range (FSR) and the finesse of at least two and wherein the first and second periodic optical filters are offset by about one quarter of the FSR.

25. The system of claim 1, wherein at least one of the first and second periodic optical filters comprises a tunable periodic optical filter.

26. The system of claim 1, wherein the optical source comprises a plurality of tunable optical sources and wherein the optical detector comprises a plurality of optical detectors, ones of which are optically coupled to respective ones of the tunable optical sources by the optical transmission path.

27. The system of claim 26, wherein the optical transmission path includes:
an optical multiplexer coupling the plurality of tunable optical sources to a source arm of the system; and
an optical demultiplexer coupling the plurality of optical detectors to a detector arm of the system.

28. The system of claim 27, further comprising a periodic optical filter in the source arm, the detector arm, a sample arm of the system and/or a reference arm of the system.

29. The system of claim 1, wherein the optical source comprises super luminescent diode sources and wherein the optical detectors comprise spectrometers, ones of which are optically coupled to a selected wavelength range emitted by the super luminescent diode sources.

30. The system of claim 29, wherein the optical transmission path includes:
an optical multiplexer coupling the super luminescent diode sources to a source arm of the system; and
an optical demultiplexer coupling the spectrometers to a detector arm of the system.

31. The system of claim 30, further comprising a periodic optical filter in the source arm, the detector arm, a sample arm of the system and/or a reference arm of the system.

32. A frequency domain optical coherence imaging system, comprising:
an optical source;
an optical detector; and an optical transmission path between the optical source and the optical detector that reduces an effective linewidth of the imaging system;

wherein the optical source comprises a plurality of optical sources and the optical detector comprises a plurality of optical detectors and wherein the optical transmission path includes an optical splitter having a first side including a port coupled to a source arm and a second side having a port coupled to a reference arm and a port coupled to a sample arm and an optical multiplexer/demultiplexer coupling the plurality of optical sources and optical detectors to the source arm;

wherein the plurality of optical sources and optical detectors comprise a plurality of optical source and detector pairs and wherein the optical transmission path further comprises a plurality of circulators coupling respective ones of the optical source and detector pairs to the optical multiplexer/demultiplexer.

* * * * *